(12) United States Patent
Jung et al.

(10) Patent No.: US 9,908,117 B2
(45) Date of Patent: Mar. 6, 2018

(54) MICROFLUIDIC SEPARATION DEVICE, SEPARATION METHOD USING THE SAME AND KIT FOR SEPARATING CIRCULATING RARE CELLS FROM BLOOD USING THE SAME

(71) Applicant: INDUSTRY-ACADEMIC COOPERATION FOUNDATION YONSEI UNIVERSITY, Seoul (KR)

(72) Inventors: Hyo Il Jung, Seoul (KR); Kyung-A Hyun, Incheon (KR); Tae Yoon Lee, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 58 days.

(21) Appl. No.: 14/861,677

(22) Filed: Sep. 22, 2015

(65) Prior Publication Data

US 2016/0082436 A1 Mar. 24, 2016

(30) Foreign Application Priority Data

Sep. 22, 2014 (KR) ........................ 10-2014-0125986

(51) Int. Cl.
*B01L 3/00* (2006.01)
*G01N 15/06* (2006.01)
(Continued)

(52) U.S. Cl.
CPC ...... *B01L 3/502761* (2013.01); *B01F 5/0647* (2013.01); *B01F 5/0655* (2013.01);
(Continued)

(58) Field of Classification Search
CPC .......... B01L 3/00; G01N 15/06; G01N 33/00; G01N 33/48
(Continued)

(56) References Cited

U.S. PATENT DOCUMENTS

| 8,277,743 | B1 * | 10/2012 | Ramberg | ............. | B01J 19/2485 |
|           |      |         |         |               | 422/129 |
| 8,430,558 | B1 * | 4/2013  | Yakhshi Tafti | ....... | B01F 5/0603 |
|           |      |         |         |               | 366/340 |

(Continued)

FOREIGN PATENT DOCUMENTS

| KR | 10-2011-0089643 A | 8/2011 |
| KR | 10-2012-0032255 A | 4/2012 |
| KR | 10-2013-0107583 A | 10/2013 |

OTHER PUBLICATIONS

KIPO Office Action for Korean Application No. 10-2014-0125986 which corresponds to the above-referenced U.S. application.
(Continued)

*Primary Examiner* — Brian J. Sines
(74) *Attorney, Agent, or Firm* — LRK Patent Law Firm

(57) ABSTRACT

The present invention relates to a microfluidic separation device, a separation method using the same and a kit for separating circulating rare cells from blood using the same, and more particularly, to a microfluidic-based separation technology for fixing target particles of a sample, which have a specific affinity for magnetic nanoparticles, to a device by use of a magnetic material, and for isolating the sample from which the target particles have been removed. The present invention may be effectively applied to remove leukocytes from a blood sample in order to isolate circulating rare cells (CRCs), particularly circulating tumor cells (CTCs).

7 Claims, 14 Drawing Sheets

(51) Int. Cl.

| | | |
|---|---|---|
| *G01N 33/00* | (2006.01) | |
| *G01N 33/48* | (2006.01) | |
| *G01N 33/543* | (2006.01) | |
| *G01N 33/50* | (2006.01) | |
| *G01N 33/569* | (2006.01) | |
| *B01F 5/06* | (2006.01) | |
| *B01F 13/00* | (2006.01) | |

(52) U.S. Cl.
CPC .... *B01F 13/0059* (2013.01); *B01L 3/502707* (2013.01); *G01N 33/5002* (2013.01); *G01N 33/5434* (2013.01); *G01N 33/54326* (2013.01); *G01N 33/54346* (2013.01); *G01N 33/56972* (2013.01); *B01L 3/5085* (2013.01); *B01L 2200/0652* (2013.01); *B01L 2200/0668* (2013.01); *B01L 2300/044* (2013.01); *B01L 2300/0858* (2013.01); *B01L 2300/0883* (2013.01); *B01L 2400/043* (2013.01); *B01L 2400/0409* (2013.01); *G01N 2333/70589* (2013.01)

(58) Field of Classification Search
USPC ......... 422/68.1, 502, 503, 504; 436/43, 180, 436/174, 177, 149, 63, 524, 518, 526, 436/529, 531; 977/773, 920, 904, 853, 977/957, 958, 959
See application file for complete search history.

(56) References Cited

U.S. PATENT DOCUMENTS

| | | | |
|---|---|---|---|
| 2007/0263477 A1* | 11/2007 | Sudarsan | B01F 5/0644 366/3 |
| 2011/0003325 A1* | 1/2011 | Durack | B01L 3/5027 435/29 |
| 2011/0008767 A1* | 1/2011 | Durack | B01L 3/5027 435/5 |
| 2011/0008818 A1* | 1/2011 | Durack | B01L 3/502753 435/29 |
| 2011/0085949 A1* | 4/2011 | Roy | B29C 71/02 422/502 |
| 2011/0127222 A1* | 6/2011 | Chang-Yen | C12M 47/04 210/695 |
| 2011/0137018 A1* | 6/2011 | Chang-Yen | G01N 35/0098 530/412 |

OTHER PUBLICATIONS

Martin A. M. Gijs, "Magnetic bead handling on-chip: new opportunities for analytical applications", Microfluid Nanofluid (2004) vol. 1, pp. 22-40, Oct. 2004.

Arjun P. Sudarsan et al., "Multivortex micromixing", PNAS, vol. 103, No. 19, pp. 7228-7233, May 2006.

* cited by examiner

| # of MCF-7 cells/ml | 50 | 100 | 500 | 1000 |
|---|---|---|---|---|
| Recovery | 91% | 92.5% | 85.3% | 89.9% |
| Purity | 0.27% | 0.85% | 2.39% | 6.09% |

FIG. 8

Separation yields of MCF-7 and Jurkat cells

| | | # of MCF-7 cells/ml | | | |
|---|---|---|---|---|---|
| | | 50 | 100 | 500 | 1000 |
| μ-MixMACS | Recovery (%) | 90.67 | 89.00 | 84.73 | 85.33 |
| | Purity (%) | 0.35 | 0.60 | 3.03 | 5.39 |
| EasySep | Recovery (%) | 54.67 | 59.00 | 75.33 | 81.30 |
| | Purity (%) | 0.25 | 0.52 | 3.62 | 6.88 |
| ΔN* | | 18 | 30 | 47 | 40.67 |

Inlet Jurkat cell concentration: $10^6$ Jurkat cells/ml

FIG. 14

MICROFLUIDIC SEPARATION DEVICE, SEPARATION METHOD USING THE SAME AND KIT FOR SEPARATING CIRCULATING RARE CELLS FROM BLOOD USING THE SAME

CROSS-REFERENCES TO RELATED APPLICATIONS

This application claims priority from Korean Application No. 10-2014-0125986, filed Sep. 22, 2014, the contents of which are incorporated herein by reference in its entirety.

BACKGROUND

1. Field of the Invention

The present invention relates to a microfluidic separation device, a separation method using the same and a kit for separating circulating rare cells from blood using the same, and more particularly, to a microfluidic-based separation technology for fixing target particles of a sample, which have a specific affinity for magnetic nanoparticles, to a device by use of a magnetic material, and for isolating the sample from which the target particles have been removed.

2. Description of Related Art

The present invention can be effectively applied to remove leukocytes from a blood sample in order to isolate circulating rare cells (CRCs), particularly circulating tumor cells (CTCs).

In general, a biochemical sample exists as a mixture of two or more components, and thus separation technology for either analyzing only a desired component in the mixture or purifying only a specific component from the mixture is very important in a sample pretreatment process. In particular, lab-on-a-chip technology for processing a small amount of a sample at high speed and with high efficiency by use of the microfluidic channel, mixer, pump, valve and the like integrated on a single chip is receiving attention.

Furthermore, cell-based diagnostics, which is important in biological or medical analysis, involves blood analysis, cell research, microbial analysis and the like. With the recent development of cell research and analysis techniques and protein and DNA analysis techniques, studies have been conducted on unify and integrate such clinical diagnostic procedures in the form of a microfluidic device.

Microfluidic technology is a technology for handling a small amount ($10^{-6}$-$10^{-12}$ liter) of a sample. It has high sensitivity despite a small sample amount, and can be easily combined with other technologies to maximize its efficiency. In addition, it is easily constructed and is inexpensive. Due to such advantages, the microfluidic technology is used in various fields.

Circulating rare cells (CRCs) are cells circulating in cells, and are very rarely present at a concentration of less than 1000 cells per ml of blood. Such circulating rare cells include circulating tumor cells (CTCs), nucleated red blood cells (nRBCs), circulating endothelial cells (CECs) and circulating stem cells (CSCs), which can be used as indicators for the early diagnosis and prognostic diagnosis of various diseases.

Particularly, in recent years, there have been increasing studies on detecting blood tumor cells, which are epithelial cells isolated from tumor, to early diagnose metastatic cancer or to monitor the results of cancer therapy. This method has the advantage of not requiring biopsy such as isolating tumor tissue directly from the body, and thus is absolutely advantageous for lung cancer patients in which tissue biopsy is difficult. However, because circulating tumor cells (CTCs) in the blood of patients are present at a very low concentration (about 1 CTC/$10^9$ blood cells), there is much difficulty in efficiently capturing and detecting the circulating tumor cells.

Korean Patent Laid-Open Publication No. 10-2013-0107583 (entitled "Composition for diagnosis of tumor cells in blood and method for detecting tumor cells in blood using the same"; published on Oct. 2, 2013) discloses a composition for diagnosis of tumor cells in blood, the composition comprising: nanoparticles having attached thereto a primary antibody such as an EpCAM antibody, which binds specifically to blood tumor cells in order to the efficiency of capture of blood tumor cells and minimize non-specific binding to blood cells to thereby increase the limit of detection; magnetic beads having a size ranging from 100 nm to 1 µm and having attached thereto a secondary antibody such as protein A, which binds to the primary antibody.

Meanwhile, a conventional magnetic-activated cell sorting (MACS) method based on magnetic nanoparticles (MNPs) is performed by mixing a magnetic particle-containing solution with a particle-containing solution using a pipette, allowing the mixture to stand for a certain time to form an MNP complex, transferring the MNP complex into a container surrounded by a magnet, and then gently sucking particles, which have not attracted to the wall surface of the container, with a pipette after a certain time. However, this conventional method has a problem in that, because it comprises multiple stages which are all performed by a manual process, particles to be sorted can be lost.

BRIEF SUMMARY

The present invention has been made in order to solve the above-described problems, and it is an object of the present invention to provide a microfluidic-based separation technology for fixing target particles of a sample, which have a specific affinity for magnetic nanoparticles, to a device by use of a magnetic material, and for isolating the sample from which the target particles have been removed.

To achieve the above object, in accordance with an embodiment of the present invention, there is provided a microfluidic separation device for forming an MNP complex comprising target particles bound to magnetic nanoparticles (MNPs) and for capturing and separating the MNP complex using a magnetic force, the microfluidic separation device comprising a mixing channel, an incubation channel and a separation channel, which are sequentially arranged to communicate with each other, wherein the mixing channel comprises at least one inlet provided upstream thereof and a wave-shaped curved channel which communicates with the inlets and which has two or more curved portions; and wherein the incubation channel comprises a first residence region having an enlarged cross-sectional area over a portion of the incubation channel; and wherein the separation channel comprises at least one magnetic material provided on one side of the separation channel, and an outlet provided downstream of the separation channel.

The mixing channel may further comprise at least one expanded channel which is formed in the curved channel and which have an expanded width over a portion of the expanded channel. The ratio of the width of the curved channel to the width of the expanded channel in the mixing channel is preferably 1:6-1:7. The expanded channel is preferably formed at 6-8 positions of the curved channel.

The expanded channel is preferably formed in the curved channel at a position at which the curved portion is shifted to the next curved portion.

The inlet of the mixing channel may comprise a magnetic nanoparticle inlet and a sample inlet. The ratio of the cross-sectional area of the first residence region in the incubation channel to the cross-sectional area of the curved channel in the mixing channel may be 1000:1-1500:1. The separation channel may comprise one or more second residence regions which have an enlarged cross-sectional area over a portion thereof and which are connected to each other in series. The separation channel preferably comprises a plurality of the magnetic materials provided on top and bottom outer surfaces of the second residence regions of the separation channel.

In accordance with another embodiment of the present invention, there is provided a separation method for forming an MNP complex comprising target particles bound to magnetic nanoparticles (MNPs) using a microfluidic separation device and for capturing and separating the MNP complex using a magnetic force, the method comprising the steps of: (S10) injecting a sample and magnetic nanoparticles into an inlet; (S20) forming the MNP complex by mixing and collision of the injected sample and magnetic nanoparticles during their flow in a mixing channel of the microfluidic separation channel; (S30) enhancing the binding force between the target particles and magnetic nanoparticles of the MNP complex while allowing the formed MNP complex to flow in an incubation channel of the microfluidic separation device; (S40) capturing the MNP complex by at least one magnetic material provided on one side of a separation channel of the microfluidic separation channel while allowing the MNP complex to flow in the separation channel; and (S50) discharging the sample, from which the MNP complex has been removed, through an outlet of the separation channel.

The mixing channel may comprise a wave-shaped curved channel having two or more curved portions such that the injected sample and magnetic nanoparticles collide with each other by first vortices formed due to the curved channel in step (S20) of forming the MNP complex.

Further, the mixing channel may further comprise at least one expanded channel, which is formed in the curved channel and has an expanded width over a portion thereof, such that the injected sample and magnetic nanoparticles collide with each other by second vortices formed due to the expanded channel in step (S20) of forming the MNP complex.

The incubation channel comprises a first residence region having an enlarged cross-sectional area over a portion thereof, such that the binding force between the target particles and magnetic nanoparticles of the MNP complex is enhanced while the formed MNP complex resides in the first residence region for a predetermined period of time in step (S30) of enhancing the binding force between the target particles and magnetic nanoparticles of the MNP complex.

In step (S10) of injecting the sample and the magnetic nanoparticles, the sample and the magnetic nanoparticles are preferably injected at a flow rate of 300-400 μl/min.

The target particles may be leukocytes, and the magnetic nanoparticles may have attached thereto an antibody (CD45 antibody) against a human leukocyte common antigen (CD45), which binds specifically bind to leukocytes, and the method may further comprise after step (S50) of discharging the sample, step (S60) of isolating circulating rare cells (CRCs) from the sample from which the MNP complex has been removed. Herein the circulating rare cells are preferably circulating tumor cells (CTCs).

In accordance with still another embodiment of the present invention, there is provided a kit for separating circulating rare cells from a blood sample, the kit comprising the microfluidic separation device as described above. In accordance with still another embodiment of the present invention, there is provided a method for fabricating a microfluidic separation device for forming an MNP complex comprising target particles bound to magnetic nanoparticles (MNPs) and for capturing and separating the MNP complex using a magnetic force, the method comprising the steps of: (a) cutting and removing a portion of a separation sheet made of polymer resin to form two or more residence regions 330 having an enlarged cross-sectional area over a portion thereof; (b) attaching a cover sheet to both sides of the separation sheet; (c) attaching to a portion of the separation sheet an incubation sheet which is made of polymer resin and which was partially cut and removed to form a first residence region having an enlarged cross-sectional area over a portion thereof; (d) attaching to the incubation sheet a mixing sheet which is made of polymer resin and which comprises at least one inlet and a curved channel communicating with the inlet and having two or more curved portions; and (e) attaching a magnetic sheet to a top and/or bottom region of the separation sheet which has formed therein the second residence portion.

Herein, each of the separation sheet, the incubation sheet and the mixing sheet is made of (meth)acrylate polymer resin, preferably polymethylmethacrylate (PMMA) resin.

In addition, step (d) may further comprise forming at least one expanded channel in the curved channel, the expanded channel having an expanded width over a portion thereof.

The microfluidic separation device of the present invention as described above, a separation method using the same, and a kit for separating circulating rare cells from blood, which comprises the same, has advantages in that, because a series of pretreatment process, including sample separation, are continuously and automatically carried out in a single microfluidic chip, the separation process can be easily performed with high efficiency and at high speed while the loss of the particles to be extracted can be minimized.

In particular, the microfluidic separation technology according to the present invention can be effectively used to remove leukocytes from blood in order to isolate circulating rare cells, particularly circulating tumor cells that are used as an indicator of various diseases.

Figure 5:
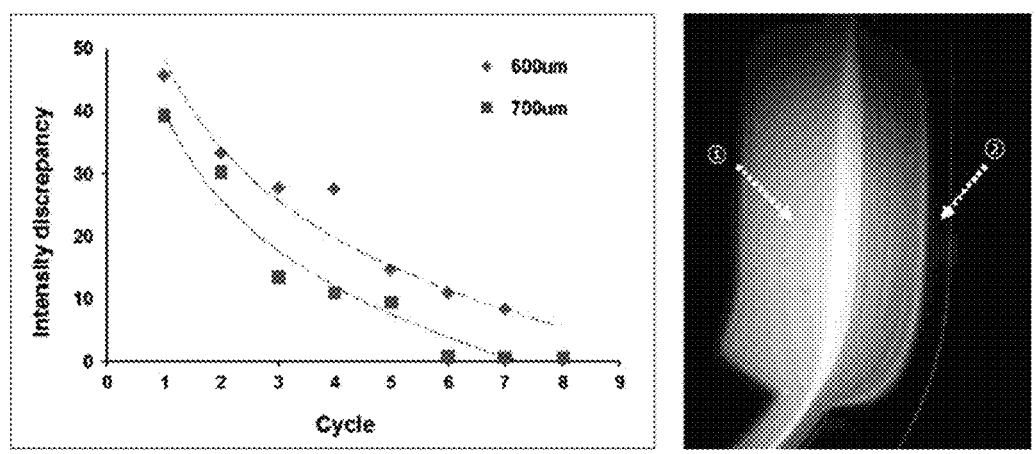

The left of FIG. 5 shows the results measured according to the experiment of Example 1, and the right of FIG. 5 is a photograph showing a state in which mixed fluids behave in the external channel 130.

Figure 6:
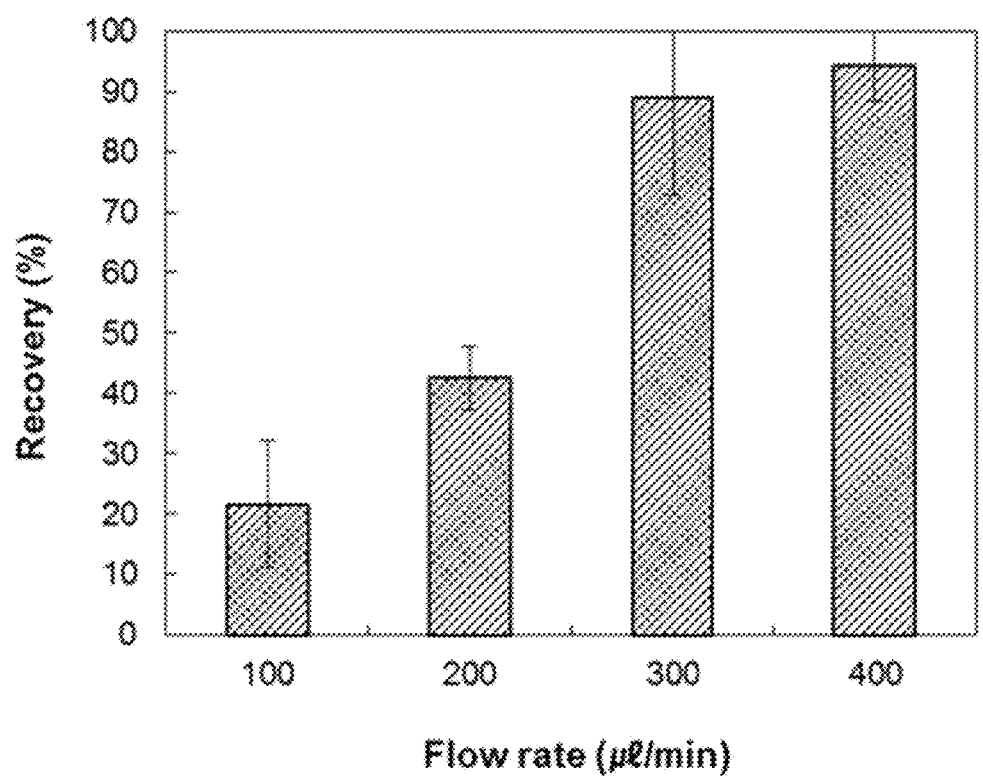

FIG. 6 is a graph showing the recovery (%) of a sample as a function of the flow rate of the sample when only the sample was injected without magnetic particles according to the experiment of Example 2.

Figure 7:
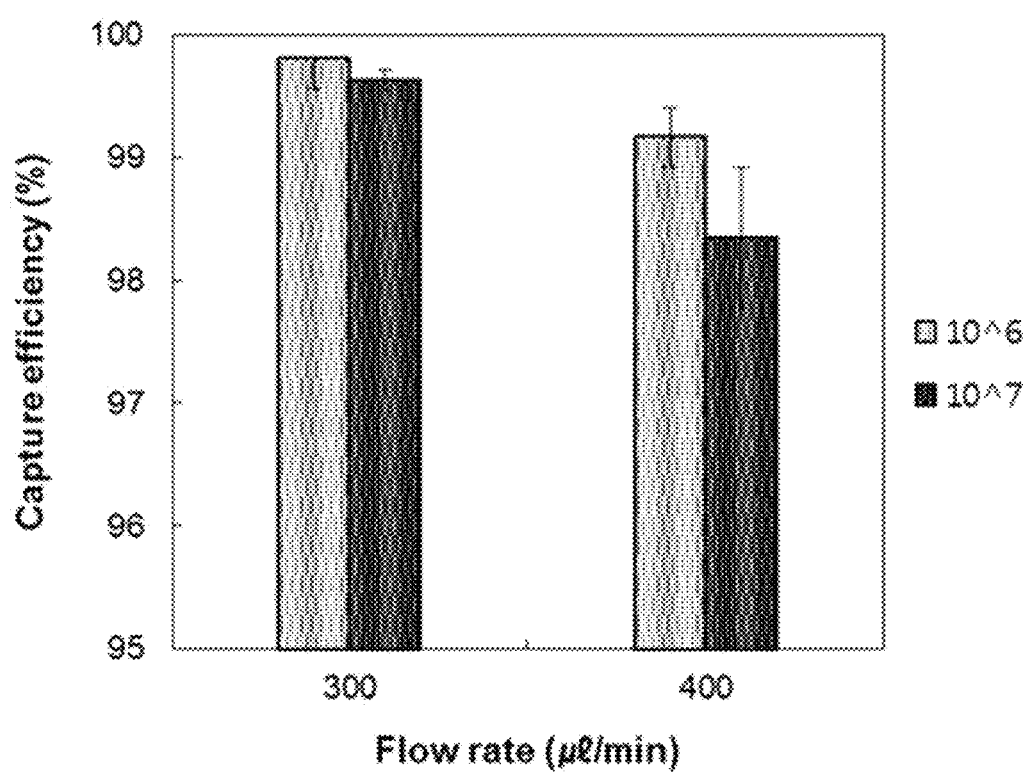

FIG. 7 is a graph showing the capture rate of leukocytes as a function of injection flow rate and leukocyte concentration, measured according to the experiment of Example 3.

FIG. 8 is a table showing the results of a spiking experiment, which show cancer cell recovery (%) and purity as a function of the number of cancer cells (MCF-7 cells) in a sample having a certain leukocyte concentration, measured according to the experiment of Example 4.

Figure 9:
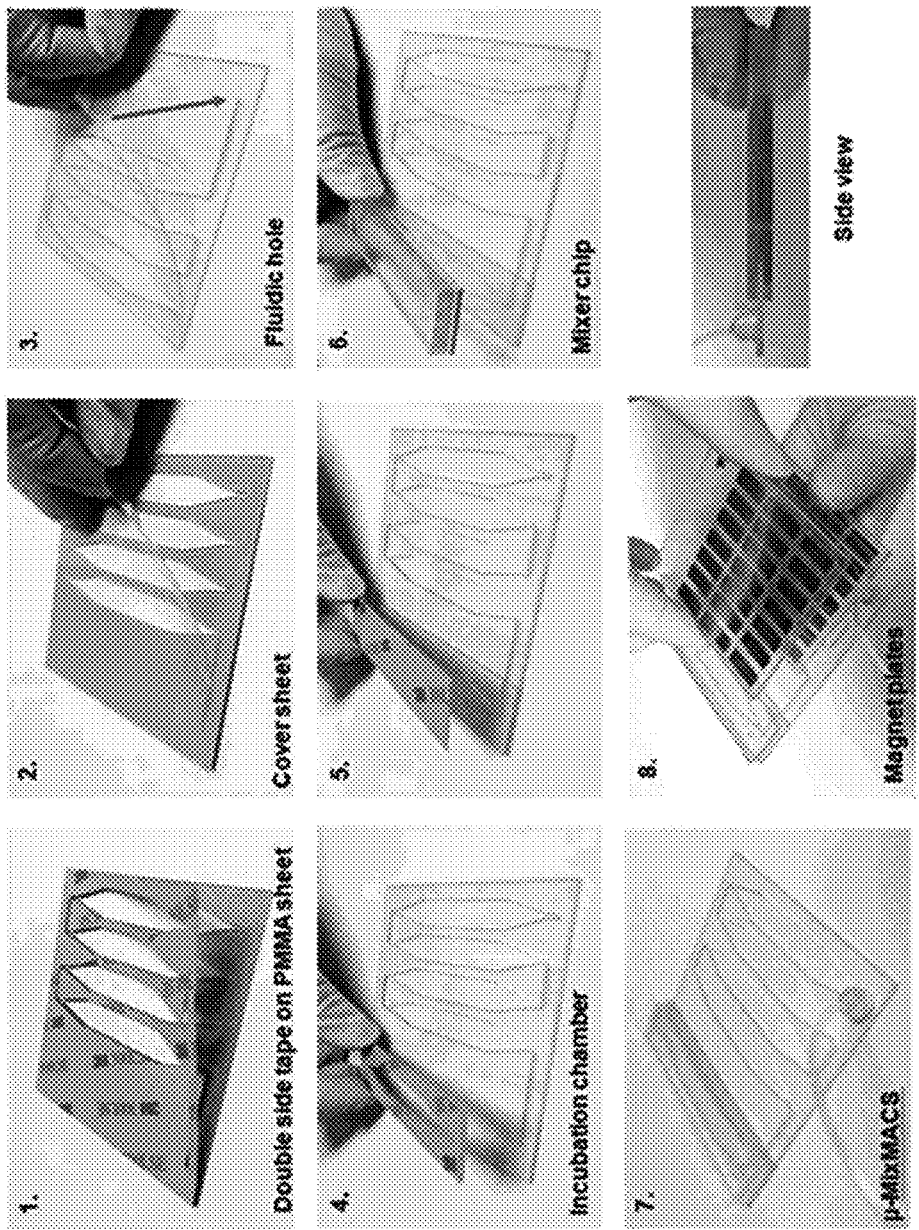

FIG. 9 depicts photographs illustrating a method for fabrication of the microfluidic separation device of the present invention in a time series sequence and a photograph showing the side view of the fabricated microfluidic separation device.

Figure 10:
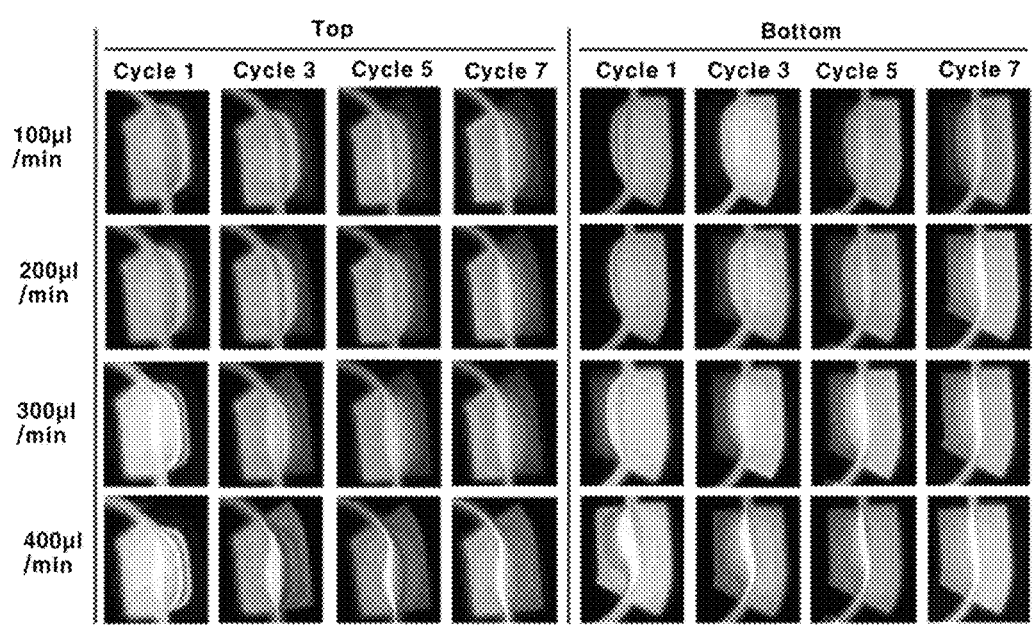

FIG. 10 depicts photographs showing the behaviors of samples in the microfluidic separation device A of the present invention at varying sample flow rates and treatment cycles.

Figure 11:
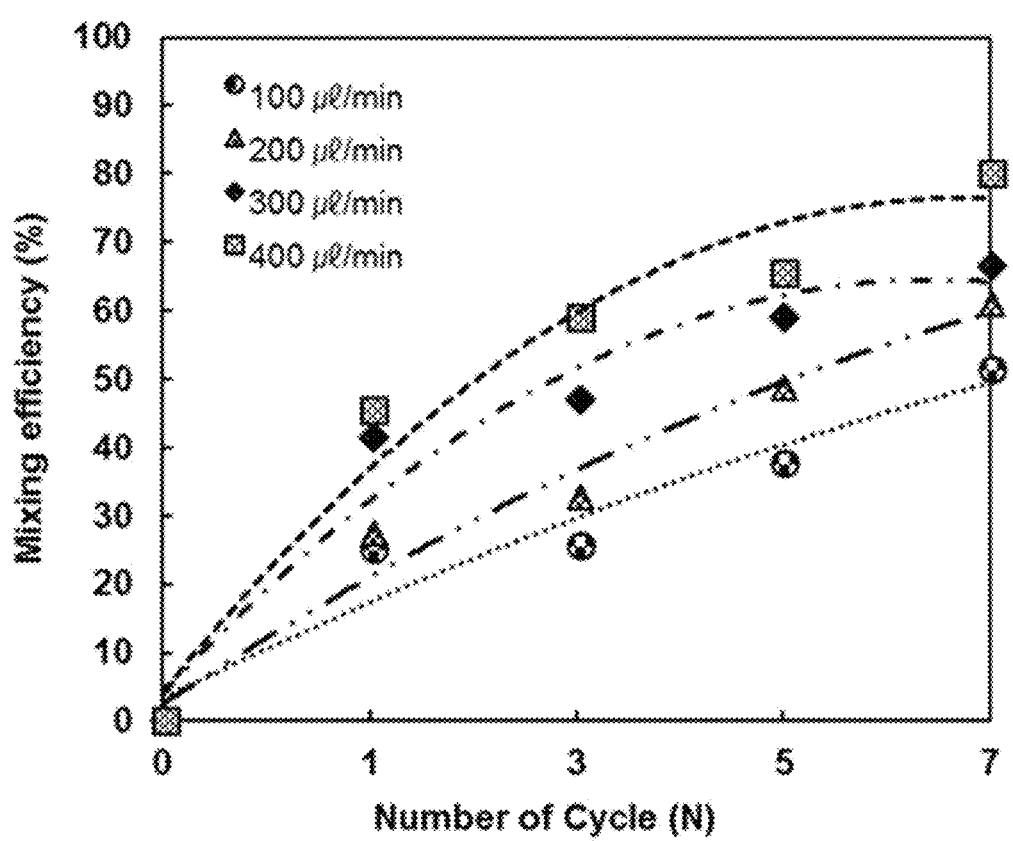

FIG. 11 is a graph numerically showing the experimental results of FIG. 10 in terms of mixing efficiency.

Figure 12:
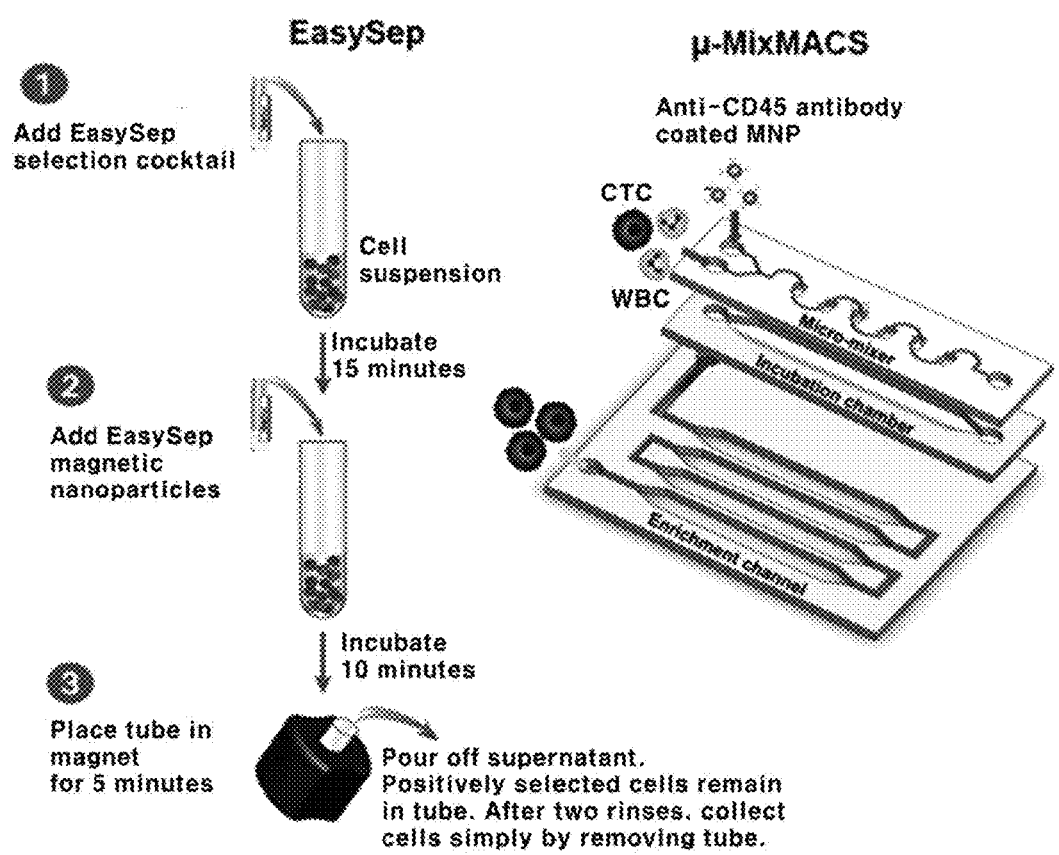

FIG. 12 is a schematic view illustrating a comparison between a Comparative Example in which mixing, incubation and separation processes are separately performed and an Example in which the microfluidic separation device of the present invention is used.

Figure 13:
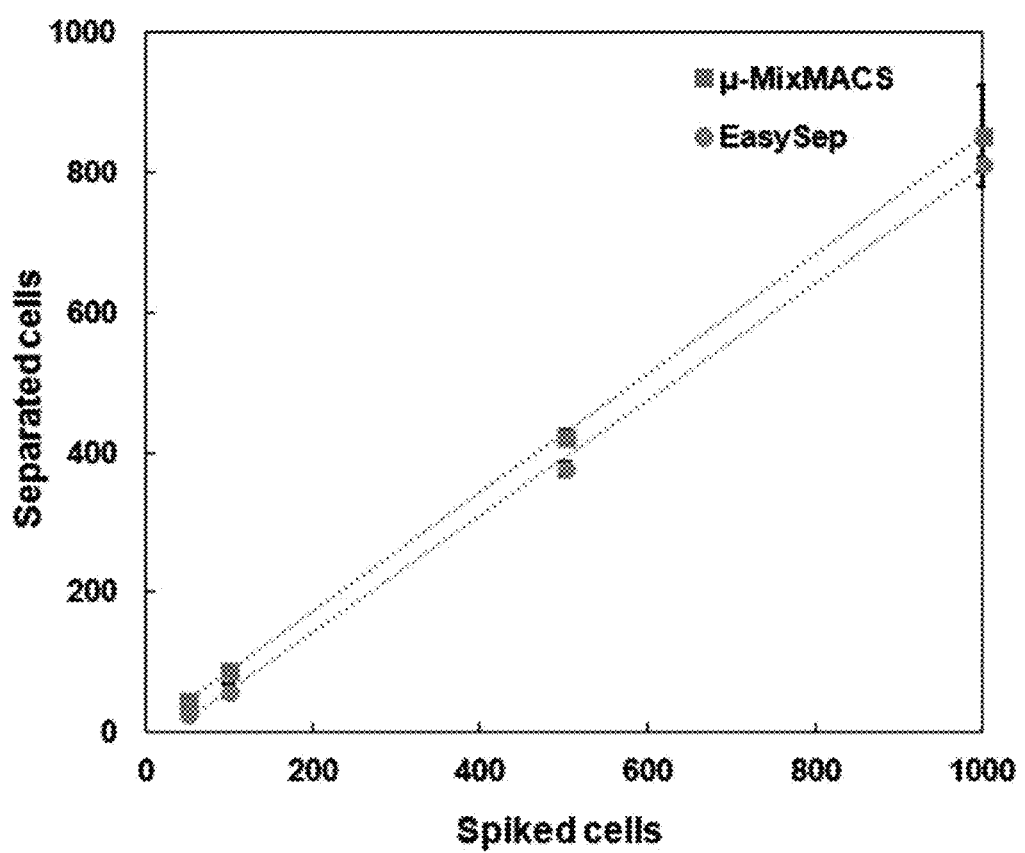

FIG. 13 is a graph illustrating experimental results showing a comparison of the ability to separate cells between a Comparative Example and an Example.

FIG. 14 is a table illustrating experimental results showing a comparison of the ability to separate cells between a Comparative Example and an Example.

DESCRIPTION OF REFERENCE NUMERALS USED IN THE DRAWINGS

A: microfluidic separation device;
B: a separation method using the microfluidic separation device;
100: mixing channel;
110: inlet;
111: magnetic nanoparticle inlet;
112: sample inlet;
120: curved channel;
121: curved portion;
130: expanded channel;
200: incubation channel;
210: first residence region;
300: separation channel;
310: magnetic material;
320: outlet;
330: second residence region.

DETAILED DESCRIPTION

Reference will be now made in detail to exemplary embodiments of the disclosure with reference to the attached drawings. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the disclosure.

Figure 1:
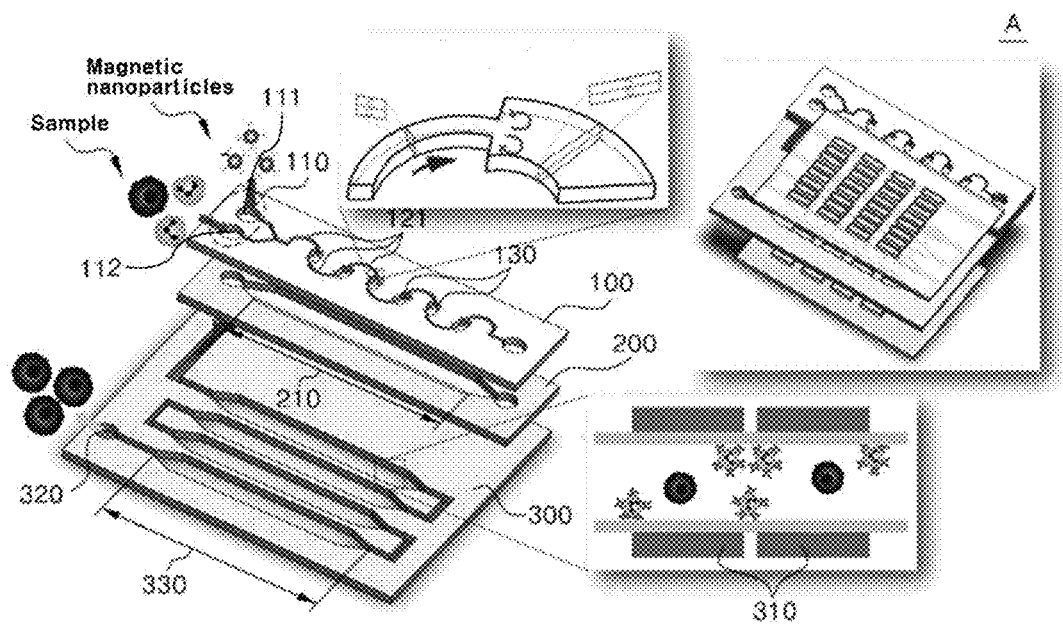
FIG. 1 is an overall schematic view of a microfluidic separation device A according to the present invention.

In accordance with an exemplary embodiment of the present invention, there is provided a microfluidic separation device A configured to form an MNP complex comprising target particles bound to magnetic nanoparticles (MNPs) and to capture and separate the MNP complex in a channel using a magnetic force. As shown in FIG. 1, the microfluidic separation device A according to the present invention is a microfluidic chip-based device comprising a mixing channel 100, an incubation channel 200 and a separation channel 300, which are sequentially arranged to communicate with one another. FIG. 1 shows an overall schematic view of the microfluidic separation device A of the present invention.

The microfluidic chip-based particle separation platform as described in the present invention can minimize the loss of particles during a separation process, compared to a conventional manual-type multistage separation platform including processes such as pipetting, sample treatment and sample container replacement. In addition, it can further reduce the loss of particles, because separation and analysis are continuously performed in a single chip unit.

Hereinafter, the overall concept of the present invention will be described in brief.

The microfluidic separation device A according to the present invention may comprise: a mixing channel 100 comprising an inlet 110 and a curved channel 120; an incubation channel comprising a first residence region 210; and a separation channel 300 comprising a magnetic material 310 and an outlet 320.

A sample and magnetic nanoparticles, which are injected into the inlet 110 of the mixing channel 100, flow in the mixing channel 100 comprising the curved channel 120 and an expanded channel 130 as described below, and are mixed and collided with each other by various vortices formed due to interactions between inertial force, centrifugal force, fluid viscosity effects and the like, to form an MNP complex. Next, when they pass through the first residence region 210 of the incubation channel 200, a residence time equal to or longer than a certain time is ensured so that the binding force between the target particles and magnetic nanoparticles of the MNP complex will further be increased. Next, the MNP complex is captured and removed in the separation channel 300 comprising the magnetic material 310, and finally, the sample from which the target particles have been removed is isolated through the outlet 320.

Hereinafter, each constituent element of the microfluidic separation device will be described in detail.

First, the mixing channel 100 is configured such that the inlet 110 is provided upstream of the channel 100 so as to communicate with the channel 100. Herein, a portion or the whole of the channel 100 may be composed of a wave-shaped curved channel 120 having formed therein a curved portion 121. As used herein, the term "curved portion 121" means a bow-shaped curved portion of any member. At least two curved portions 121 may be connected to each other to form the wave-shaped curved channel 120.

In the curved channel 120, first vortices, particularly Dean vortices, are formed in the vertical plane due to interactions between inertial force, centrifugal force fluid viscosity force, etc., thereby promoting the mixing and collision of the fluids on the vertical plane.

The angle (θ) at which the curved portion 121 of the curved channel 120 is formed means an angle bent from the start point (at which the straight channel starts to be curved) of the curved portion 121 to the end point (at which the channel is changed again to the straight channel) of the curved portion 121. The curved portion 121 may be formed at an angle between about 130° and about 180°. Most preferably, the curved portion 121 is formed at an angle of 130° in order to effectively form Dean vortices to the highest possible degree using inertial force, centrifugal force, etc.

Meanwhile, one or more expanded channels 130 may be intermittently provided in the curved channel 120 of the mixing channel 100. The expanded channel 130 means a channel region having an expanded width. When the mixed sample enters the orifice-shaped expanded channel 130, second vortices, particularly expansion vortices, are formed in the horizontal plane due to the abruptly expanded width of the channel, thereby promoting the mixing and collision of the fluids on the horizontal plane. As described above, due to the first vortices (Dean vortices) on the horizontal plane in the wave-shaped curved channel 120 and the second vortices (expansion vortices) on the horizontal plane in the expanded channel 130, the mixing, collision and binding between the injected sample and magnetic nanoparticles effectively occur. In order to optimally generate the expansion vortices, the ratio of the width ($D_1$) of the curved channel 120 to the width ($D_2$) of the expanded channel 130, ($D_1:D_2$), is preferably 1:6 to 1:7.

Figure 2:
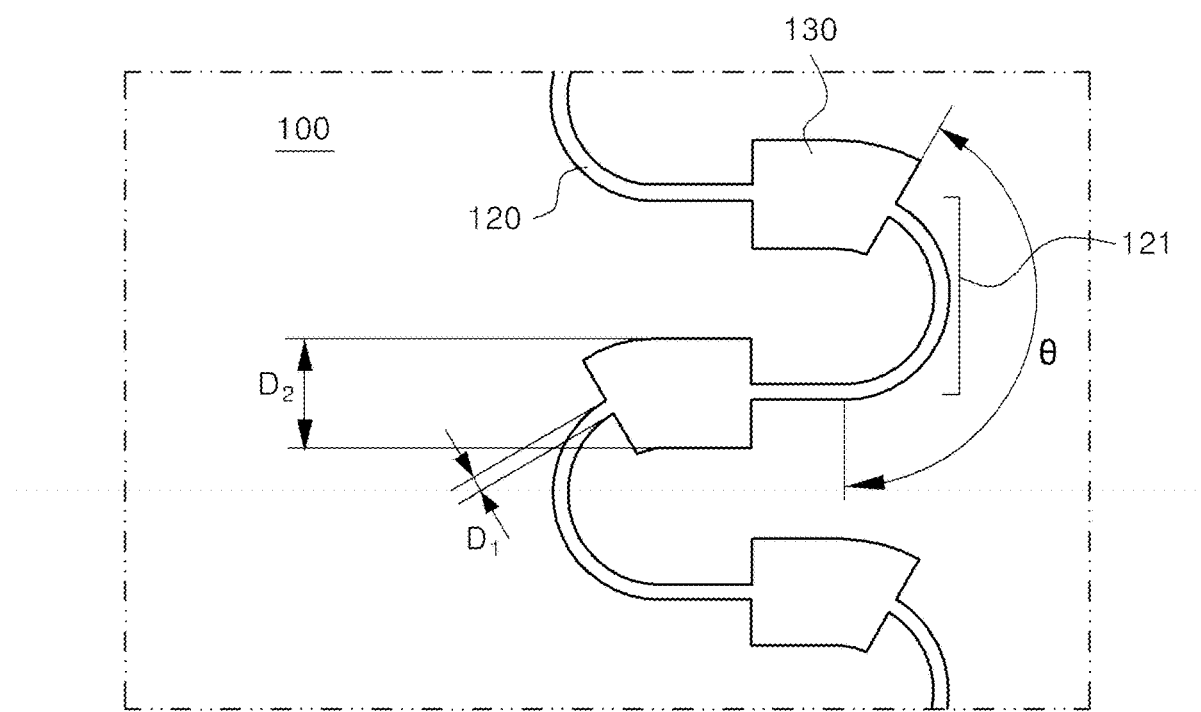
FIG. 2 is a schematic view of a mixing channel 100 having formed therein a curved channel 120 and an expanded channel 130.

FIG. 2 shows a schematic view of the mixing channel 100 having formed therein the curved channel 120 and the expanded channel 130 according to the present invention. When the curved channels 120 are connected to form a wave shape while the expanded channel 130 is intermittently formed at a position near the straight channel, at which the curved direction of the curved portion 121 is changed, the synergistic effect between the first vortices and the second vortices can be best exhibited. The behavior of the fluid in the mixing channel 100 is controlled such that the Reynolds number of the fluid is greater than 1. This is advantageous in terms of mixing and binding. The expanded channel 130 in the curved channel 120 is preferably formed at 6-8 positions, as supported by the experimental results described in the Examples below.

Figure 3:
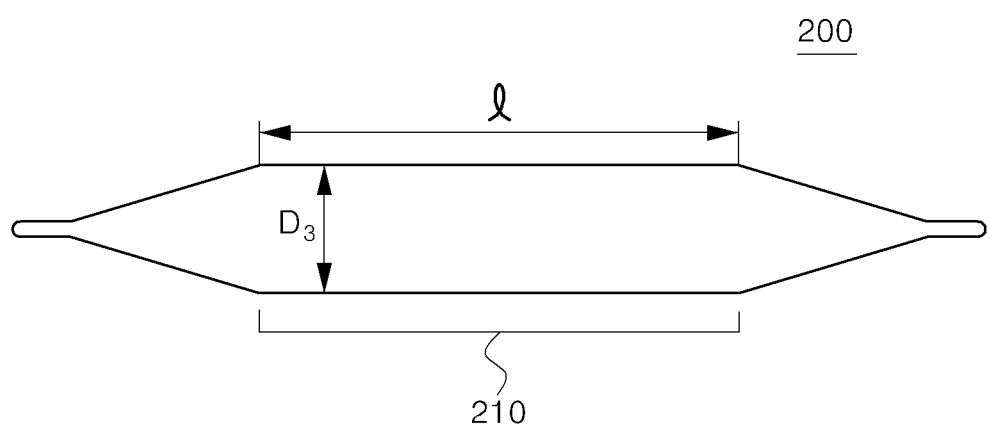
FIG. 3 is a schematic view of an incubation channel 200 according to the present invention.

Meanwhile, the incubation channel 200 is a channel connected downstream of the mixing channel 100. As shown in FIG. 3, in the incubation channel 200, a first residence region 210 having an enlarged cross-sectional area is formed over a portion of the incubation channel 200. This enables a certain residence time and residence space to be ensured in order to increase the binding force between the magnetic nanoparticles and the target particles, before the MNP complex is finally removed using the magnetic material 310. FIG. 3 shows a schematic view of the incubation channel 200 according to the present invention.

In order to maximize the residence effect as described above, the ratio of the cross-sectional view ($S_1$) of the first residence portion 210 of the incubation channel 200 to the cross-sectional area ($S_2$) of the curved channel 120 of the mixing channel, ($S_1:S_2$), is preferably 1000:1 to 1500:1. In addition, in order to ensure a sufficient residence time and residence space, the first residence portion 210 preferably has a length of 30-40 mm.

Finally, the separation channel 300 is connected downstream of the incubation channel 200, and may provided with a magnetic material 310 for capturing the MNP complex and an outlet 320 for discharging the treated sample. The MNP complex formed upstream of the separation channel 300 is captured and removed by a plurality of the magnetic materials 310 provided on one side of the separation channel 300, preferably the top and bottom outer surfaces of the separation channel 300, thereby obtaining the sample from which the MNP complex has been removed.

The configuration (physical property) of the separation channel 300 is preferably identical or similar to that of the incubation channel 200. In order to ensure a certain residence time and residence space in the separation channel 300, similar to those in the incubation channel 200, to thereby increase the efficiency with which the MNP complex is separated, one or more second residence portions 330, each having an enlarged cross-sectional area over a portion thereof, are preferably configured to be connected in series to each other. Herein, a plurality of the magnetic materials 310 may be provided at the top, bottom, or both of the second residence regions 330

The microfluidic separation device A according to the present invention can be fabricated by combining the three microfluidic chips with one another by a simple adhesive means such as a double-sided tape without using an external jig, and thus is inexpensive and easy to fabricate. In addition the microfluidic separation device A has advantages in that, because three functions are achieved in a single chip unit, the loss of sample particles can be minimized, unlike the conventional technique in which sample particles are lost during pipetting, sample container replacement and the like, and processes from sample pretreatment to final sample separation can be completed within a short time.

Figure 4:
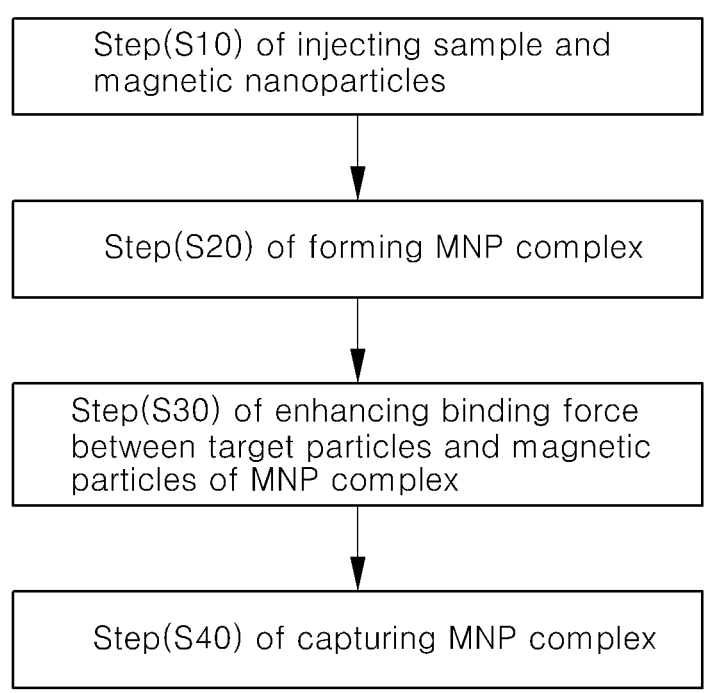
FIG. 4 is a flowchart of a separation method B using the microfluidic separation device of the present invention.

In accordance with another exemplary embodiment of the present invention, there is provided a separation method B for forming an MNP complex comprising target particles bound to magnetic nanoparticles using the microfluidic separation device A and for capturing and separating the MNP complex using a magnetic force. FIG. 4 shows a flowchart of the separation method B according to the present invention. The separation method B according to the present invention may generally comprise the steps of: (S20) injecting a sample and magnetic nanoparticles; (S20) forming an MNP complex; (S30) enhancing the binding force between the target particles and the magnetic nanoparticles in the MNP complex; and (S40) capturing the MNP complex.

Step (S10) of injecting the sample and the magnetic nanoparticles is a step of injecting the sample and the magnetic nanoparticles into the inlet 110 of the microfluidic separation device A. Herein, the inlet 110 may comprise a magnetic nanoparticle inlet 111 and a sample inlet 112, which are separately provided. The sample and the magnetic nanoparticles are injected at a flow rate of 300-400 μl/min as supported by the experimental results described in the Examples below.

The fluids injected through the inlet 110 flow in the mixing channel 100 of the microfluidic separation device A while they are mixed and collided with each other to form an MNP complex (step S20). In this step, as mentioned above, vortices are formed through the curved channel 120 and the expanded channel 130 to promote the mixing and collision of the fluids.

The formed MNP complex flows in the incubation channel 200 of the microfluidic separation device A while a sufficient residence time and residence space for the MNP complex are ensured to enhance the binding force between the target particles and magnetic nanoparticles of the MNP complex (step S30). As already mentioned above, this process is achieved through the first residence region 210 of the incubation channel 200.

When the MNP complex having an enhanced binding force flows the separation channel 300 of the microfluidic separation device A, it is captured and removed by the magnetic material 310 provided in the separation channel 300, and finally, the sample from which the MNP complex has been removed is discharged through the outlet 320 (step S50).

As described above, the target particles to be removed are bound to the magnetic nanoparticles and captured and removed by the magnetic material 310, thereby isolating the sample from which the target particles have been removed. Herein the target particles to be separated or isolated may be either target particles that are bound to the magnetic nanoparticles, or particles in the sample from the target particles have been removed. In the former case, a subsequent process for separately isolating the MNP complex captured by the magnetic material 310 and separating the magnetic nanoparticles therefrom should be performed. In the latter case, the target particles can be obtained without a separate subsequent process by isolating the sample discharged through the outlet 320.

The microfluidic separation device A and separation method B of the present invention may be used to isolate circulating rare cells (CRCs), particularly circulating tumor cells, CTCs), from a blood sample.

In this case, the target particles may be leukocytes, and an antibody (CD45 antibody) against a human leukocyte common antigen (CD45), which binds specifically to leukocytes, may be attached to the magnetic nanoparticles. Thus, leukocytes can bind to the CD45 antibody-attached magnetic nanoparticles to form an MNP complex, and thus can be effectively removed, thereby isolating circulating tumor cells.

In accordance with still another exemplary embodiment of the present invention, there is provided a kit for separating circulating rare cells from a blood sample, the kit comprising the microfluidic separation device A as described above.

In accordance with still another exemplary embodiment of the present invention, there is provided a method for fabricating the microfluidic separation device A as described above. Hereinafter, the fabrication method if the present invention will be described in detail with reference to FIG. 9.

The fabrication method of the present invention may comprise the steps of: (a) preparing a separation sheet made of polymer resin; (b) attaching a cover sheet to both sides of the separation sheet; (c) attaching an incubation sheet to a portion of the separation sheet; (d) attaching a mixing sheet to the incubation sheet; and (e) attaching a magnetic sheet to the top and/or bottom of the separation sheet.

Specifically, in the present invention, the separation sheet, the incubation sheet and the mixing sheet may be made of (meth)acrylate-based polymer resin, preferably polymethylmethacrylate (PMMA) resin In step (a) of preparing the separation sheet in which the separation channel 300 is formed, second residence regions 330, a channel for connecting the second residence regions in series, a sample inlet and a sample outlet are formed on a polymer resin substrate. The region in which the channel is formed can be cut and removed as shown in FIG. 9, thereby preparing the separation sheet.

Next, step (b) of attaching a cover sheet to both sides of the prepared separation sheet is performed to provide a space in which the sample flows in the channel. The cover sheet can be attached by various known methods. Preferably, it can be attached to both sides of the separation sheet using a tape. Attachment of the cover sheet should be performed such that it communicates to the sample inlet and outlet formed on the separation sheet.

Next, in step (c) of attaching the incubation sheet, the incubation sheet is attached to a portion of the separation sheet so that it communicates to the sample inlet side provided on the separation sheet. The incubation sheet may also be made of PMMA resin. It can be prepared by cutting and removing PMMA resin from the region in which the first residence region 210 is to be formed, similar to the case of the separation sheet. The prepared incubation sheet can be attached to a portion of the separation sheet using an adhesive tape.

Next, step (d) of attaching the mixing sheet is a step of attaching the prepared mixing sheet to the incubation sheet. As mentioned above, the mixing sheet has formed therein a mixing channel 100 comprising at least one inlet 110 and a wave-shaped curved channel 120 that communicates with the inlet 110 and that has at least two curved portions 121 formed therein.

Next, a magnetic sheet comprising a plurality of magnetic materials 310 is attached to the top, bottom, or both of a separation sheet portion to which the incubation sheet and the mixing sheet were not attached (i.e., a separation sheet portion in which the second residence region 330 was formed). In this way, the microfluidic separation device A according to the present invention can be fabricated.

The method for fabricating the microfluidic separation device A according to the present invention has advantages in that it can be performed by a simple operation using easily available materials and in that the efficiency of the device can be maximized while minimizing the size or thickness of the device as shown in FIG. 9.

Hereinafter, examples of the microfluidic separation device of the present invention, a separation method using the device, and a kit for separating circulating rare cells from blood, which comprises the device, will be described. However, these examples are merely embodiments of the present invention and do not represent the technical spirit of the present invention. Therefore, it should be understood that various equivalents and variations capable of substituting for these examples may exist at the time of filing the application.

Example 1

Experiment on Efficiency of Mixing Channel 100

A simulated experiment was performed to examine the efficiency of mixing of a sample and magnetic nanoparticles as a function of the difference in width between the curved channel 120 and the expanded channel 130.

Specifically, the curved channel 120 was formed with a width of 0.1 mm and a curved angle ($\theta$) of 150°, and a plurality of expanded channels 130 were formed at points at which the curved portions 121 of the curved channel 120 were shifted. All the channels were formed to have the same height of 40 μm. Next, using 7 μm green fluorescent particles (simulated sample; portion ② in FIG. 5) and an orange fluorescent fluid (stimulated magnetic nanoparticles; portion ① in FIG. 5), the difference in intensity between the two colors in the channel was measured using Image J program.

The left of FIG. 5 shows the results of the measurement, and the right of FIG. 5 is a photograph showing a state in which the mixed fluids flow in the expanded channel 130. As shown therein, when the flow rate was 100 μl/min (Re=37), the expanded channels 130 having a width of 0.7 mm showed a mixing efficiency close to 100% in $6^{th}$ cycle (i.e., when the fluid passed through six expanded channels 130), whereas the expanded channels 130 having a width of 0.6 mm showed a mixing efficiency similar thereto from $8^{th}$ cycle.

Example 2

Experiment on Recovery (%) as a Function of Flow Rate Upon Injection of Sample Alone without Magnetic Nanoparticles FIG. 6 is a graph showing the recovery (%) of a sample as a function of injection flow rate when only the sample was injected without magnetic nanoparticles. The reason why this experiment was performed is because an object of the present invention is to remove the target particles to be removed, by attaching them to a chip using magnetic nanoparticies, and to stably discharge the target particles to be extracted, unbound to the magnetic nanoparticles, from the device.

Regarding the dimensions of the microfluidic separation device A used in this experiment, the mixing channel 100 was formed in the same manner as described in Example 1 (the expanded channel 130 having a width of 0.7 mm). In the incubation channel 200, the first residence region 210 was formed to have a width of 8 mm, a height of 0.7 mm and a length of 30 mm, and in the separation channel 300, four second residence regions 330, each having the same dimensions of the first residence region of the incubation channel 200, were configured to be connected in series.

Through this experiment, a sample recovery of 90% or higher was shown at a flow rate of 300 μl/min or higher.

Example 3

Experiment on Capture Rate of Leukocytes as a Function of Flow Rate and Cell Concentration An experiment was performed by injecting CD45 antibody-conjugated magnetic nanoparticles and a blood sample, allowing leukocytes in the blood sample to bind to the magnetic nanoparticles and to be attached to the chip, and measuring the amount of leukocytes in the finally discharged sample. Variables were injection flow rate (μl/min) and the leukocyte concentration (cells/ml) of the sample injected. The dimensions of the microfluidic separation device A used in this experiment were the same as those in Example 2.

FIG. 7 is a graph showing the capture rate of leukocytes as a function of injection flow rate and leukocyte concentration. As shown therein, at a flow rate of 300 μl/min, a leukocyte capture rate of 99% or higher appeared even at a high cell concentration of $10^7$ cells/me, but at a flow rate of 400 μl/min, leukocytes were discharged through the outlet 320 due to high flow rate without being captured.

Example 4

Experiment on Spiking of Cancer Cells and Leukocytes

FIG. 8 is a table showing spiking experiment results indicating cancer cell recovery and purity as a function of the number of cancer cells (MCF-7 cells) in a sample having a certain leukocyte concentration. Specifically, 50, 100, 500 and 1000 cancer cells were spiked into samples containing leukocytes at a concentration of $10^6$ cells/ml, and were separated using the microfluidic separation device A of the present invention. The dimensions of the microfluidic separation device A used in the present invention were the same as those in Example 2.

It was shown that 80% or more of the cancer cells were recovered and the cancer cells could be separated with a high purity of up to 6.09%.

Example 5

Experiment on Comparison of Mixing Efficiency as a Function of Flow Rate of Sample and Number of Cycles FIGS. 10 and 11 show the results of an experiment performed to compare mixing efficiency as a function of the flow rate of a sample in the device and the number of cycles. Specifically, while the flow rate of a sample flowing in the mixing channel 100 was set at 100, 200, 300 and 400 μl/min and the number of cycles was changed from 1 to 7, the sample behavior appearing in the top and bottom of the channel was observed and the efficiency of separation was calculated.

As can be seen in FIGS. 10 and 11, as the flow rate of the sample flowing in the mixing channel 100 was gradually increased to a level of about 400 μl/min, the generation of vortices became more active, resulting in an increase in mixing efficiency. In addition, it could be seen that, as the number of cycles, that is, the number of the expanded channels 130 provided in the mixing channel 100, increased, mixing efficiency also increased. Moreover, as the flow rate of the sample was further increased, problems associated with the durability of the separation device occurred, the possibility for the sample to be lost or for the device to be broken increased. In addition, as the number of the expanded channels 130 was closer to 7, the graph of FIG. 11 became slower, suggesting that an increase in mixing efficiency is insignificant when the expanded channel 130 is provided at 7-8 or more positions.

Example 6

Experiment on Comparison of Separation Ability Between a Method in which Each Step is Separately Carried Out (Comparative Example) and the Method of the Present Invention (Example)

FIG. 12 is a schematic view illustrating a comparison between a method in which each of mixing, incubation and separation steps is separately carried out (Comparative Example) and a method in which all the steps are continuously and sequentially carried out in a single device using the microfluidic separation device A of the present invention.

Referring to FIGS. 13 and 14 which show a comparison of the cell separation ability between the Comparison Example and the Example, it can be seen that the cell separation ability was better in the Example than in the Comparative Example, in addition to the fact that the Example has advantages over the Comparative Example in that the separation process is easier and the loss of the sample is minimized. Specifically, it can be seen that the cell recovery was higher in the Example than in the Comparative Example regardless of the number of the spiked cells, and the number (ΔN) of the separated cells was also larger in the Example than in the Comparative Example.

Further, the embodiments discussed have been presented by way of example only and not limitation. Thus, the breadth and scope of the invention(s) should not be limited by any of the above-described exemplary embodiments, but should be defined only in accordance with the following claims and their equivalents. Moreover, the above advantages and features are provided in described embodiments, but shall not limit the application of the claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," the claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in the claims found herein. Furthermore, any reference in this disclosure to "invention" in the singular should not be used to argue that there is only a single point of novelty claimed in this disclosure. Multiple inventions may be set forth according to the limitations of the multiple claims associated with this disclosure, and the claims accordingly define the invention(s), and their equivalents, that are protected thereby. In all instances, the scope of the claims shall be considered on their own merits in light of the specification, but should not be constrained by the headings set forth herein.

What is claimed is:

1. A microfluidic separation device for forming a magnetic nanoparticle (MNP) complex comprising target particles bound to MNPs and for capturing and separating the MNP complex using a magnetic force, the microfluidic separation device comprising:
   a mixing channel, an incubation channel and a separation channel, which are sequentially arranged to communicate with each other,
   wherein the mixing channel comprises:
   at least one inlet provided upstream of the mixing channel; and
   a curved channel which is wave-shaped, communicates with the at least one inlet, and has two or more curved portions,
   wherein the incubation channel comprises a first residence region having an enlarged cross-sectional area over a portion of the incubation channel, and
   wherein the separation channel comprises:
   an outlet provided downstream of the separation channel;
   a plurality of second residence regions which are connected to each other in series and have an enlarged cross-sectional area over a portion of the separation channel to ensure a predetermined residence time and residence space of the MNP complex; and
   a plurality of magnetic materials provided on top and bottom outer surfaces of the second residence regions.

2. The microfluidic separation device of claim 1, wherein the mixing channel further comprises at least one expanded channel which is formed in the curved channel and which have an expanded width over a portion of the at least one expanded channel.

3. The microfluidic separation device of claim 2, wherein in the mixing channel, a ratio of a width of the curved channel to a width of the expanded channel is 1:6-1:7.

4. The microfluidic separation device of claim 2, wherein the at least one expanded channel formed in the curved channel includes six to eight expanded channels.

5. The microfluidic separation device of claim 2, wherein the at least one expanded channel is formed in the curved channel at a position at which one of the curved portions is shifted to a next one of the curved portions.

6. The microfluidic separation device of claim 1, wherein the at least one inlet of the mixing channel comprises a magnetic nanoparticle inlet and a sample inlet.

7. The microfluidic separation device of claim 1, wherein a ratio of a cross-sectional area of the first residence region of the incubation channel to across-sectional area of the curved channel of the mixing channel is 1000:1-1500:1.

* * * * *